(12) United States Patent
Cohn

(10) Patent No.: US 7,079,898 B2
(45) Date of Patent: Jul. 18, 2006

(54) PAIN RELIEVING AND HEALING DEVICE

(76) Inventor: Salomon Cohn, 625 Arguello Blvd. Apt 101, San Francisco, CA (US) 94118

( * ) Notice: Subject to any disclaimer, the term of this patent is extended or adjusted under 35 U.S.C. 154(b) by 778 days.

(21) Appl. No.: 10/302,699

(22) Filed: Nov. 25, 2002

(65) Prior Publication Data

US 2004/0102822 A1    May 27, 2004

(51) Int. Cl.
*A61H 7/00* (2006.01)

(52) U.S. Cl. .................. 607/45; 607/1; 607/3; 607/63; 601/9; 601/18; 601/97

(58) Field of Classification Search .................. 607/45, 607/3, 1, 63, 96; 601/9, 15, 18, 84, 89, 97, 601/100, 107, 108; 600/26, 27
See application file for complete search history.

(56) References Cited

U.S. PATENT DOCUMENTS 4,088,128 A * 5/1978 Mabuchi ...................... 601/101
5,377,701 A * 1/1995 Fang ........................... 132/271

* cited by examiner

*Primary Examiner*—Kennedy Schaetzle

(57) ABSTRACT

Pain Relieving and Healing Device with a rigid tubular member being relatively open at the forward use end and closed by an end plate at the rear end. The inside of the tube contains a rigid piston slidably fitting within the inside diameter of the tube and an attached motor and gear assembly for driving the piston between two and five cycles per second. The piston has embedded within it a heat source and a heat radiating plate. The piston capable of traveling at various speeds by use of a solid state motor speed circuit. A preferred embodiment includes a timer circuit and associated LCD display for tracking the time for each healing session.

6 Claims, 3 Drawing Sheets

PAIN RELIEVING AND HEALING DEVICE

CROSS REFERENCE TO RELATED APPLICATIONS

Not Applicable

STATEMENT REGARDING FEDERALLY SPONSORED RESEARCH OR DEVELOPMENT

Not Applicable

DESCRIPTION OF ATTACHED APPENDIX

Not Applicable

BACKGROUND OF THE INVENTION

This invention relates generally to the field of non-invasive healing devices for human or animal use and more specifically to a hand held pain relieving and healing device.

For thousands of years, people have sought relief from aches, pains and other internal abnormalities that may cause discomfort.

Many modalities of healing have evolved by members of various healing and medical professions. In my career as a professional in the healing arts I have experimented with many traditional and non-traditional healing modalities including Reiki, Reflexology, Deep Massage Therapy, Hypnotherapy and Time Line Therapy. I also have earned a Doctor of Philosophy Degree in Psychology. While many of the healing modalities I have experimented with have shown various degrees of success, I was not fully satisfied with their results.

In my own healing work I have discovered that by applying a reciprocating motion with the palm of my hand while the hand is face down, parallel and in close proximity to the skin surface of a patient, a soothing healing effect is produced in the area. I have noticed that a reciprocating hand motion of approximately two to five cycles per second produces a small breeze of air from the downward motion to be applied to the patients skin and the upward motion creates a slight vacuum that draws the air under my hand up and away. In this way I can slowly move my hand over the portions of the patient's body while all the time creating an up and down motion with my hand as described above until the patient feels some relief in the location of discomfort. I believe that the combination of intermittent breeze and heat from my hand produces a healing effect. Unfortunately, this mode of healing can be somewhat taxing on the practitioner in that the repetitive reciprocal motion of the hand over long periods of time can cause muscle fatigue. There is therefore a need for a device that can produce the above described effect in a way that is less fatiguing on the practitioner.

BRIEF SUMMARY OF THE INVENTION

The primary object of the invention is to provide a device that, non-invasively, relieves pain and promotes healing in an individual.

Another object of the invention is to provide a healing device that is portable and can be used in a variety of applications.

Another object of the invention is to provide a healing device that can be easily held by a practitioner.

A further object of the invention is to provide a healing device that uses an in and out piston motion to propel and retract heated air onto the portion of a person's body that needs healing or pain relief.

Other objects and advantages of the present invention will become apparent from the following descriptions, taken in connection with the accompanying drawings, wherein, by way of illustration and example, an embodiment of the present invention is disclosed.

In accordance with a preferred embodiment of the invention, there is disclosed a Pain Relieving and Healing Device comprising: a rigid tubular member approximately two inches in outside diameter and eight inches long, said tubular member being relatively open at the forward use end and closed by an end plate at the rear end, the inside of said tube containing a rigid piston slidably fitting within the inside diameter of said tube and an attached motor and gear assembly for driving said piston forwards and backwards approximately one and one half inches at a speed of between two and five cycles per second, said piston having embedded within it a heat source and a heat radiating plate, and said piston capable of traveling at various speeds by use of a solid state motor speed circuit.

BRIEF DESCRIPTION OF THE DRAWINGS

The drawings constitute a part of this specification and include exemplary embodiments to the invention, which may be embodied in various forms. It is to be understood that in some instances various aspects of the invention may be shown exaggerated or enlarged to facilitate an understanding of the invention.

DETAILED DESCRIPTION OF THE PREFERRED EMBODIMENTS

Detailed descriptions of the preferred embodiment are provided herein. It is to be understood, however, that the present invention may be embodied in various forms. Therefore, specific details disclosed herein are not to be interpreted as limiting, but rather as a basis for the claims and as a representative basis for teaching one skilled in the art to employ the present invention in virtually any appropriately detailed system, structure or manner.

Figure 1:
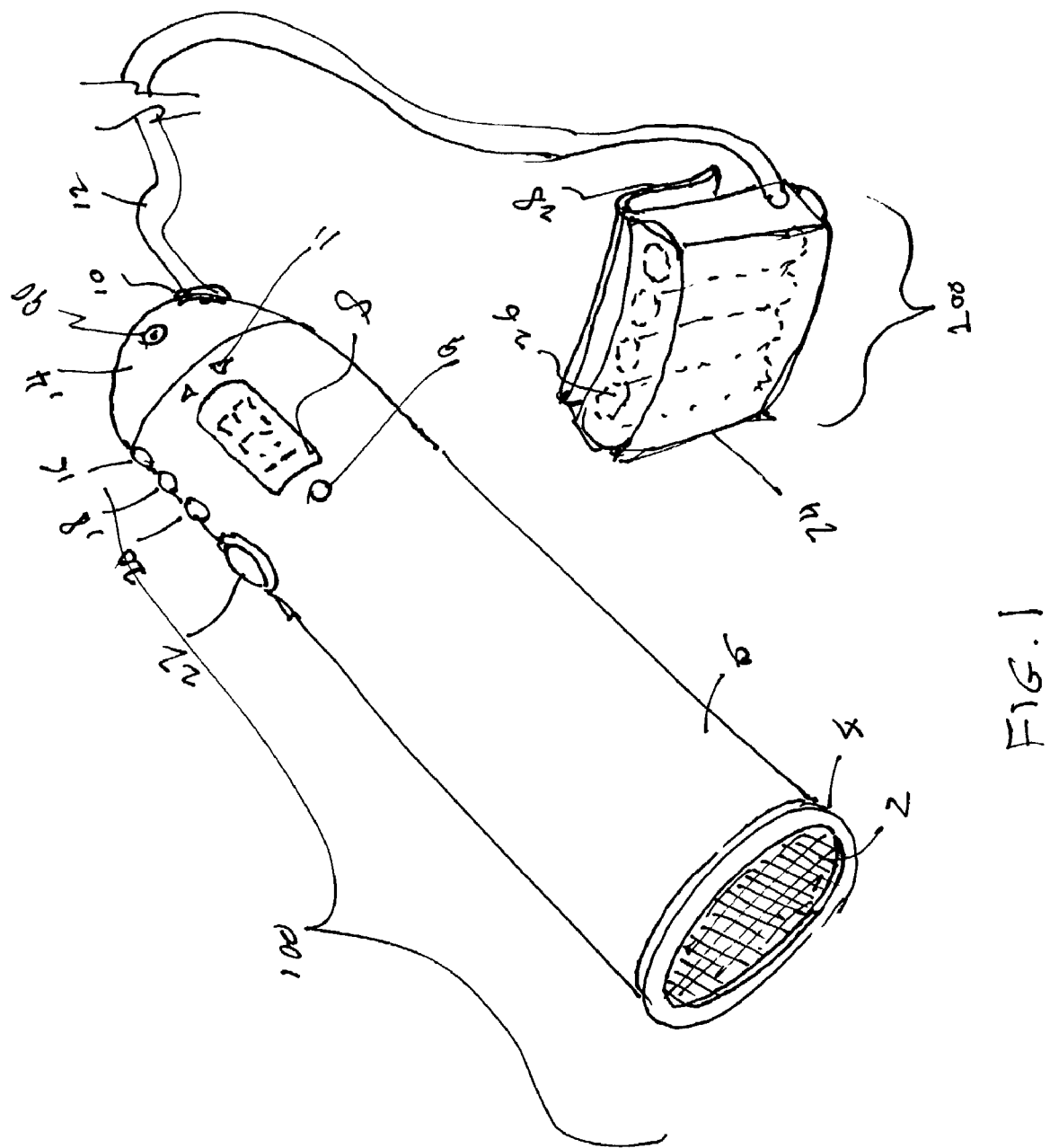
FIG. 1 is a perspective view of the present invention.

Referring now to FIG. 1 we see a perspective view of the healing device of the present invention 100. and associated battery pack assembly 200. The device 100 is constructed of a rigid tube 6 made of metal or plastic. The tube is relatively open at the front end and covered with a screen element 2 that is supported by a frame 4. The rear end of tube 6 is covered by end cap 14. Control switches 16, 18, 20, 22 help operate the device 100 as will be explained below. An LCD timer 8 operated by buttons 9, 11 help tell the user how long he or she has used the device 100. A power cord 12 emits from strain relief aperture 10 and terminates in a battery pack assembly 200. Batteries 26 are inserted into housing 24. A belt clip 28 allows the pack 200 to attach to the user's belt. An alternate power source can be a wall pack transformer that is plugged at one end to socket 90 and at the opposite end to a standard wall outlet located in a home or office or the like. The diameter of the Tube is approximately two inches and can be comfortably grasped by the user. The length of the tube 6 is approximately eight inches.

Figure 2:
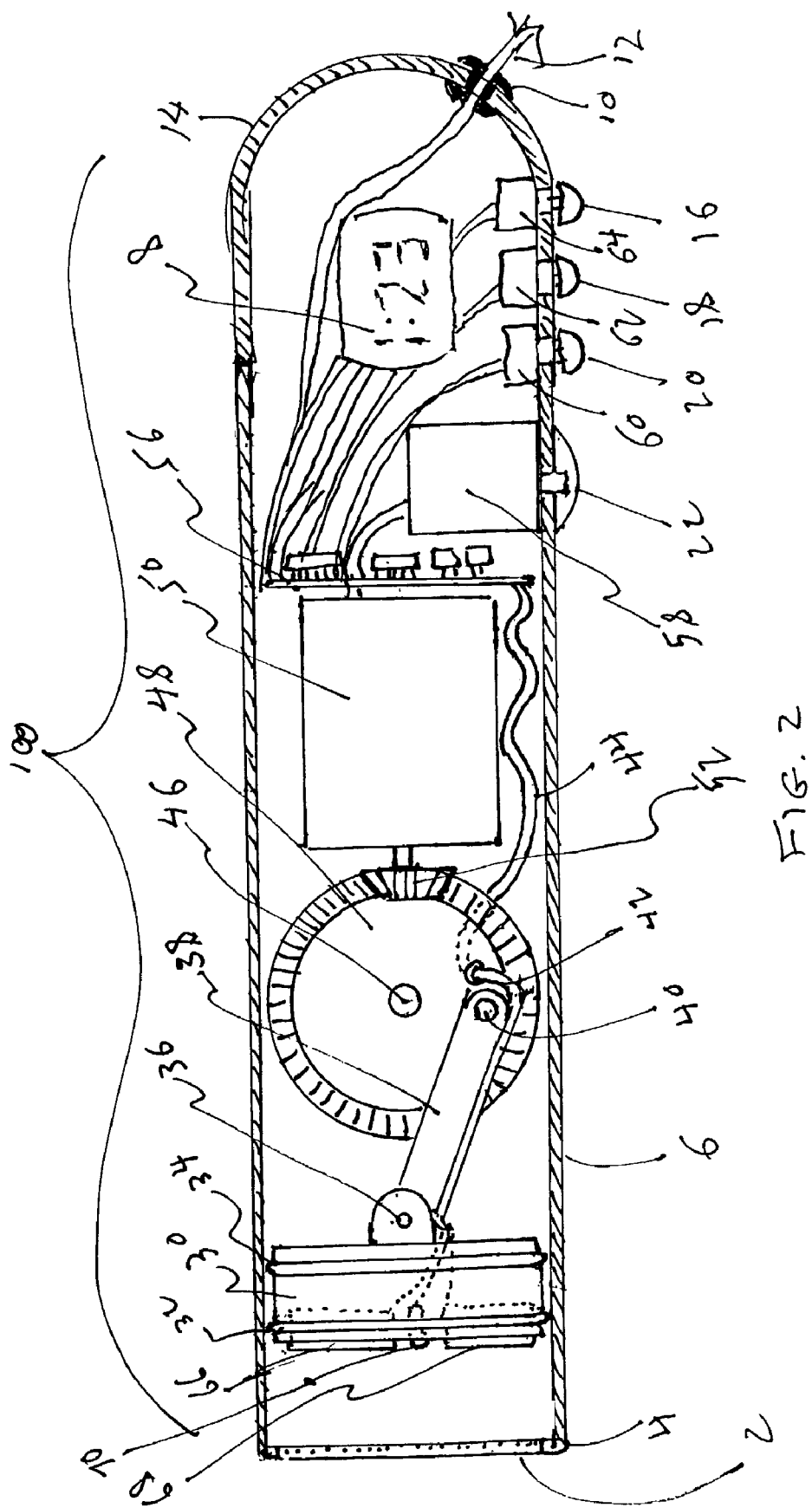
FIG. 2 is a side section view of the present invention.

FIG. 2 shows a side section view of the present invention. A piston 30 is powered by a gear reduced motor assembly 50. A miter gear 52 powers larger miter gear 48. A pinned strut 38 revolves around shaft 46. The opposite end of strut 38 is attached to clevis 36 so that as gear 48 rotates, strut 38 draws piston 30 in and out approximately one and one half inches. O rings 32, 34 surround piston 30 so that there is a relatively snug fit between the piston and the inside diameter of tube 6. Therefore, when piston 30 is drawn in, it also draws local air into the front of tube 6. On the outward stroke, piston 30 pushes air out. Piston 30 containers a heat source 66, 68. In the described embodiment the heat source is a pair of ceramic resistors 66, 68. Piston 30 also holds an LED 70 that can illuminate the area being worked on by a practitioner. Speed control circuit 56 and potentiometer 58 can vary the speed of motor drive 50 so that piston 30 runs between two and five cycles per second. Rotary knob 22 controls speed. Switch 60 turns heat source 66, 68 on and off. Switch 62 turns LED 70 on and off. switch 64 turns motor 50 on and off. LCD timer 8 is of standard design and can be used by the practitioner to check time spent on a patient.

Figure 3:
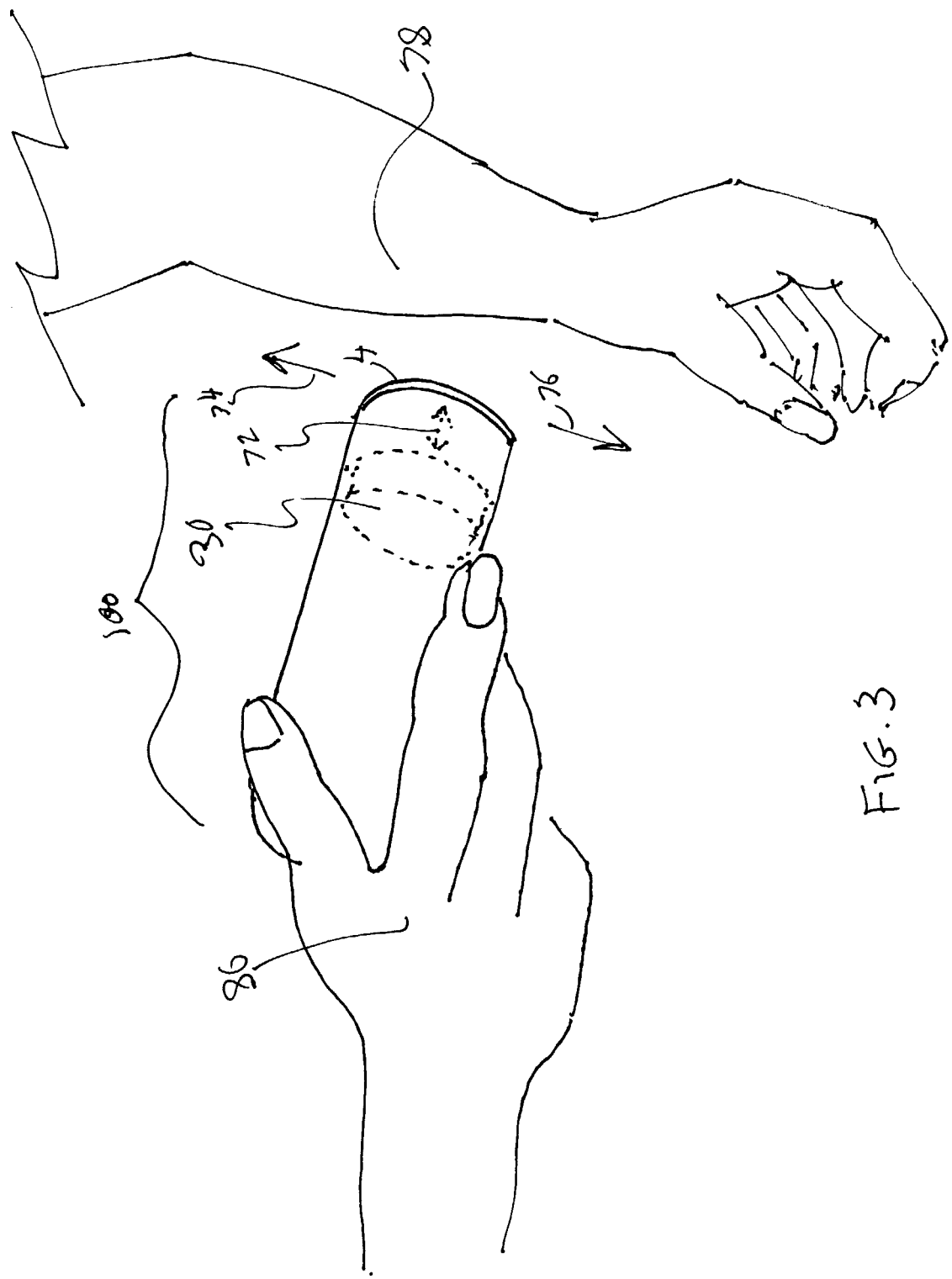
FIG. 3 is a perspective view of a person using the present invention.

FIG. 3 shows a person using the present invention 100. A practitioner 86 is holding the unit 100 so that the front of the device 100 is approximately one inch from the patients body part 78. Piston 30 travels in and out approximately one and one half inch as shown by arrows 72. The practitioner slowly moves the device 100 over the body part to be treated as shown by arrows 74, 76. This motion pumps warm air onto the the area to be treated 78 and alternately draws the air into the front of the device. This air pumping action duplicates and replaces the palm pumping activity that is currently used by healing practitioners thereby reducing the fatigue that can be experienced from practicing the manual palm pumping process.

While the invention has been described in connection with a preferred embodiment, it is not intended to limit the scope of the invention to the particular form set forth, but on the contrary, it is intended to cover such alternatives, modifications, and equivalents as may be included within the spirit and scope of the invention as defined by the appended claims.

What is claimed is:

1. Pain Relieving and Healing Device comprising:
    a rigid tubular member approximately two inches in outside diameter and eight inches long;
    said tubular member being relatively open at the forward use end and closed by an end plate at the rear end;
    the inside of said tube containing a rigid piston slidably fitting within the inside diameter of said tube and an attached motor and gear assembly for driving said piston between two and five cycles per second;
    said piston having embedded within it a heat source and a heat retaining plate; said front opening of said tube covered by a screen material to prevent a person from touching said heat source; and
    said piston capable of traveling at various speeds by use of a solid state motor speed circuit.

2. Pain Relieving and Healing Device as claimed in claim 1 further comprising a timer circuit and associated LCD display for tracking the time for each healing session.

3. Pain Relieving and Healing Device as claimed in claim 1 further comprising an LED light source also embedded into the forward surface of said piston.

4. Pain Relieving and Healing Device as claimed in claim 1 wherein said drive motor and said heater can be powered by a battery pack or by a wall pack transformer and standard voltage and current found in a house or office.

5. Pain Relieving and Healing Device as claimed in claim 1 wherein said piston drive motor, said heater source and said LED are activated and deactivated by external switches.

6. Pain Relieving and Healing Device as claimed in claim 1 wherein said piston includes at least one O ring mounted around said piston's perimeter to insure that as much air as possible is drawn into the said tube and pushed out of the said tube by said piston.

* * * * *